(12) United States Patent
Steenbakkers-Menting et al.

(10) Patent No.: US 12,291,627 B2
(45) Date of Patent: May 6, 2025

(54) PROPYLENE-BASED TERPOLYMER COMPOSITION FOR PIPES

(71) Applicant: SABIC GLOBAL TECHNOLOGIES B.V., Bergen op Zoom (NL)

(72) Inventors: Henrica Norberta Alberta Maria Steenbakkers-Menting, Geleen (NL); Tinashe Victor Mandishonha Ndoro, Geleen (NL); Desiree Marie Louise Seegers, Geleen (NL); Erik Delsman, Geleen (NL); Raymond Gerlofsma, Geleen (NL); Tim Kiggen, Geleen (NL); Martin Alexander Zuideveld, Geleen (NL); Akhlaq Moman, Geleen (NL); Patrick Elisabeth Luc Voets, Geleen (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 962 days.

(21) Appl. No.: 17/263,338

(22) PCT Filed: Jul. 22, 2019

(86) PCT No.: PCT/EP2019/069640
§ 371 (c)(1),
(2) Date: Jan. 26, 2021

(87) PCT Pub. No.: WO2020/020811
PCT Pub. Date: Jan. 30, 2020

(65) Prior Publication Data
US 2021/0214540 A1    Jul. 15, 2021

(30) Foreign Application Priority Data
Jul. 27, 2018   (EP) .................................... 18185950

(51) Int. Cl.
*C08L 23/12*    (2006.01)
*G01N 33/44*    (2006.01)

(52) U.S. Cl.
CPC ............ *C08L 23/12* (2013.01); *G01N 33/442* (2013.01); *C08L 2203/18* (2013.01)

(58) Field of Classification Search
None
See application file for complete search history.

(56) References Cited

U.S. PATENT DOCUMENTS

| | | |
|---|---|---|
| 4,579,836 A | 4/1986 | Azoumanidis et al. |
| 8,017,206 B2 * | 9/2011 | De Palo .................... B32B 1/08 |
| | | 525/240 |
| 8,785,584 B2 | 7/2014 | Cavalieri et al. |
| 8,993,703 B2 | 3/2015 | Marzolla et al. |
| 9,006,368 B2 | 4/2015 | Marzolla et al. |
| 9,487,649 B2 | 11/2016 | Galvan et al. |
| 9,988,523 B2 | 6/2018 | Tranninger et al. |
| 10,316,123 B2 | 6/2019 | Destro et al. |
| 11,407,867 B2 | 8/2022 | Massari et al. |
| 2007/0196608 A1 * | 8/2007 | De Palo ................. B32B 27/32 |
| | | 428/36.92 |
| 2014/0332109 A1 * | 11/2014 | Cavalieri ................ B32B 27/32 |
| | | 138/140 |
| 2014/0378602 A1 * | 12/2014 | Walther .............. C08L 23/0807 |
| | | 525/240 |
| 2015/0299445 A1 | 10/2015 | Cavalieri et al. |
| 2015/0322179 A1 | 11/2015 | Galvan et al. |

(Continued)

FOREIGN PATENT DOCUMENTS

| | | |
|---|---|---|
| EP | 2653496 A1 | 10/2013 |
| EP | 3064548 A1 | 9/2016 |

(Continued)

OTHER PUBLICATIONS

Escher et al.; "Carbon Nuclear Magnetic Resonance of Ethylene-Propylene-1-hexene Terpolymers"; Journal of Polymer Science: Part A: Polymer Chemistry, vol. 42; 2004; pp. 2474-2482.

(Continued)

*Primary Examiner* — Anthony J Frost

(74) *Attorney, Agent, or Firm* — CANTOR COLBURN LLP

(57) ABSTRACT

The invention relates to a polypropylene composition comprising a terpolymer composition comprising (A) a first terpolymer fraction containing propylene, ethylene and 1-hexene, wherein the first terpolymer fraction has a melt flow rate of 0.005 to 0.20 dg/min determined by ISO 1133-1:2011 (230° C., 2.16 kg) and (B) a second terpolymer fraction containing propylene, ethylene and 1-hexene, wherein the second terpolymer fraction has a melt flow rate of 0.30 to 70 dg/min determined by ISO 1133-1:2011 (230° C., 2.16 kg), wherein the first terpolymer fraction is prepared using a first set of reaction conditions, the second terpolymer fraction is prepared using a second set of reaction conditions and the first and second set of reaction conditions are different, wherein the polypropylene composition (i) has a melt flow rate of 0.10 to 0.70 dg/min determined by ISO 1133-1:2011 (230° C., 2.16 kg), (ii) has a content of ethylene derived units in the range from 1.6 to 3.0 wt %; (iii) has a content of 1-hexene derived units in the range from 1.7 to 4.0 wt %; and (iv) has a ratio of the content of ethylene derived units to the content of 1-hexene derived units in the composition of at least 0.70.

18 Claims, No Drawings

(56) References Cited

U.S. PATENT DOCUMENTS

| | | |
|---|---|---|
| 2016/0145365 A1 | 5/2016 | Destro et al. |
| 2017/0327613 A1 | 11/2017 | Ciarafoni et al. |
| 2021/0292448 A1 | 9/2021 | Steenbakkers-Menting et al. |

FOREIGN PATENT DOCUMENTS

| | | | |
|---|---|---|---|
| WO | 2006002778 A1 | 1/2006 | |
| WO | 2013083575 A1 | 6/2013 | |
| WO | WO-2018011177 A1 * | 1/2018 | ............... G01N 3/08 |
| WO | 2018059955 A1 | 4/2018 | |

OTHER PUBLICATIONS

International Search Report; International Application No. PCT/EP2019/069640; International Filing Date: Jul. 22, 2019; Date of Mailing: Aug. 20, 2019; 3 pages.

Written Opinion; International Application No. PCT/EP2019/069640; International Filing Date: Jul. 22, 2019; Date of Mailing: Aug. 20, 2019; 5 pages.

* cited by examiner

PROPYLENE-BASED TERPOLYMER COMPOSITION FOR PIPES

This application is a National Stage application of PCT/EP2019/069640, filed Jul. 22, 2019, which claims the benefit of European Application No. 18185950.5, filed Jul. 27, 2018, both of which are incorporated by reference in their entirety herein.

The invention relates to a polypropylene composition comprising a terpolymer composition, to the use of the polypropylene composition and to articles, preferably pipes, comprising the polypropylene composition.

Polypropylene-based polymers have many characteristics which make them suitable for many applications, for instance pipes such as hot and cold water pressure pipes. For hot and cold water pressure pipes, it is especially important that such pipes show a long time to brittle failure especially at elevated temperatures in combination with a good impact resistance and a good flexural modulus. The long time to brittle failure is necessary to ensure the lifetime of the pipe during use. A good impact resistance is very important during the handling (installation, transportation etc) of the pipe.

Attempts have been made to achieve favorable properties by using different types of comonomers and varying process conditions.

Use of propylene/ethylene/1-hexene terpolymers is known in the art for the production of pipes. For example WO2006/002778 relates to a pipe system comprising a terpolymer of propylene/ethylene and alpha olefin wherein the ethylene content is from 0 to 9% by mol, preferably from 1 to 7% by mol and the 1-hexene content ranges from 0.2 to 5% wt. WO2013/083575 discloses a terpolymer containing propylene, ethylene and 1-hexene wherein: (i) the content of 1-hexene derived units ranges from 1 wt % to 3.2 wt %, (ii) the content of ethylene derived units is higher than 1.4 wt % and C2 content <C6 content −0.2, further defined by the MFR and the melting temperature.

There is still a need in the art for a propylene-based terpolymer composition having an improved impact resistance while maintaining a long time to brittle failure and a good flexural modulus.

It is an objective of the present invention to provide a propylene/ethylene/1-hexene terpolymer composition having an improved impact resistance while maintaining a long time to brittle failure and a good flexural modulus.

Accordingly, the invention provides a polypropylene composition comprising a terpolymer composition comprising (A) a first terpolymer fraction containing propylene, ethylene and 1-hexene, wherein the first terpolymer fraction has a melt flow rate of 0.030 to 1.0 dg/min determined by ISO 1133-1:2011 (230° C., 5 kg) and (B) a second terpolymer fraction containing propylene, ethylene and 1-hexene, wherein the second terpolymer fraction has a melt flow rate of 0.30 to 70 dg/min determined by ISO 1133-1:2011 (230° C., 2.16 kg), wherein the first terpolymer fraction is prepared using a first set of reaction conditions, the second terpolymer fraction is prepared using a second set of reaction conditions and the first and second set of reaction conditions are different, wherein the polypropylene composition
  (i) has a melt flow rate of 0.10 to 0.70 dg/min determined by ISO 1133-1:2011 (230° C., 2.16 kg);
  (ii) has a content of ethylene derived units in the range from 1.6 to 3.0 wt %;
  (iii) has a content of 1-hexene derived units in the range from 1.7 to 4.0 wt %; and
  (iv) has a ratio of the content of ethylene derived units to the content of 1-hexene derived units of at least 0.70.

It was surprisingly found that the polypropylene composition according to the invention comprising two types of terpolymer fractions with different MFRs each containing ethylene and 1-hexene results in a pipe having a good balance of the time to brittle failure and flexural modulus (stiffness) and show an increase in impact resistance.

The term "pipe" as used herein also includes pipe fittings, valves and all parts which are commonly necessary for e.g. a hot water piping system. Also included within the definition are single and multilayer pipes, where for example the pipe may include one or more metal layers and may include one or more adhesive layers.

(A) First Terpolymer Fraction

The first terpolymer fraction has a melt flow rate of 0.030 to 1.0 dg/min, for example 0.10 to 0.60 dg/min, determined by ISO 1133-1:2011 (230° C., 5 kg).

Preferably, the content of ethylene derived units in the first terpolymer fraction in the composition according to the invention is 0.50 to 4.0 wt %, for example 1.0 to 3.0 wt %.

Preferably, the content of 1-hexene derived units in the first terpolymer fraction in the composition according to the invention is 1.0 to 6.0 wt %, for example 1.5 to 5.0 wt %.

Preferably, the ratio of the content of ethylene derived units to the content of 1-hexene derived units in the first terpolymer fraction in the composition according to the invention is at least 0.10, preferably at least 0.20, more preferably at least 0.30, and preferably at most 1.5, preferably at most 1.4.

(B) Second Terpolymer Fraction

The second terpolymer fraction has a melt flow rate of 0.30 to 70 dg/min, for example 1.0 to 30 dg/min, determined by ISO 1133-1:2011 (230° C., 2.16 kg).

Preferably, the content of ethylene derived units in the second terpolymer fraction in the composition according to the invention is 1.0 to 6.0 wt %, for example 2.0 to 5.0 wt %.

Preferably, the content of 1-hexene derived units in the second terpolymer fraction in the composition according to the invention is 0.5 to 4.0 wt %, for example 1.0 to 3.0 wt %.

Preferably, the ratio of the content of ethylene derived units to the content of 1-hexene derived units in the second terpolymer in the composition according to the invention is at least 0.70, preferably at least 0.80, more preferably at least 0.90, and preferably at most 5.0, preferably at most 4.0.

Terpolymer Composition

The terpolymer composition in the polypropylene composition according to the invention may comprise polymer fractions other than the first terpolymer fraction and the second terpolymer fraction. Preferably however, the terpolymer composition according to the invention does not comprise polymer fractions other than the first terpolymer fraction and the second terpolymer fraction. Preferably, the total of the first terpolymer fraction and the second terpolymer fraction is at least 80 wt %, preferably at least 90 wt %, at least 95 wt %, at least 98 wt %, at least 99 wt % or 100 wt % of the polymer fractions in the terpolymer composition in the polypropylene composition according to the invention. Preferably, the total of the first terpolymer fraction and the second terpolymer fraction is at least 80 wt %, preferably at least 90 wt %, at least 95 wt %, at least 98 wt %, at least 99 wt % or 100 wt % of the terpolymer composition in the polypropylene composition according to the invention.

Preferably, the amount of the first terpolymer fraction is in the range from 20 to 85 wt % based on the terpolymer composition and the amount of the second terpolymer fraction is in the range from 80 to 15 wt % based on the terpolymer composition, for example the amount of the first terpolymer fraction is in the range from 40 to 85 wt % based on the terpolymer composition and the amount of the second terpolymer fraction is in the range from 15 to 60 wt % based on the terpolymer composition.

In preferred embodiments, the amount of the first terpolymer fraction is in the range from 20 to 85 wt %, preferably from 40 to 85 wt % based on the terpolymer composition and the amount of the second terpolymer fraction is in the range from 80 to 15 wt %, preferably from 15 to 60 wt % based on the terpolymer composition, wherein the total amount of first terpolymer fraction and second terpolymer fraction is 100 wt % based on the terpolymer composition.

Polypropylene Composition

The polypropylene composition of the invention may further comprise additives. Preferably, the polypropylene composition according to the invention does not comprise polymers other than the terpolymer composition. Preferably, the sum of the amount of the terpolymer composition and the additives is 100 wt % based on the polypropylene composition. More preferably, the sum of the amount of the first terpolymer fraction and the second terpolymer fraction and the additives is 100 wt % based on the polypropylene composition.

Additives suitable for use in pipes include but are not limited to nucleating agents, stabilizers, anti-oxidants pigments and/or colorants, impact modifiers, flame retardants, acid scavengers, anti-microbials and the like. Such additives are well known in the art. The skilled person will choose the type and amount of additives such that they do not detrimentally influence the aimed properties of the composition.

Preferably, the amount of the additive in the composition is chosen from 0 to 5 wt % based on the total weight of the polypropylene composition (the polypropylene composition comprises 95 to 100 wt % of the terpolymer composition), preferably the amount of additive is from 0.01 to 3 wt %, for example from 0.1 to 2 wt %, based on the total weight of the polypropylene composition.

The polypropylene composition according to the invention has a melt flow rate of 0.10 to 0.70 dg/min, preferably 0.10 to 0.50 dg/min, more preferably 0.10 to 0.30 dg/min, more preferably as determined by ISO 1133-1:2011 (230° C., 2.16 kg).

The content of ethylene derived units in the polypropylene composition according to the invention is 1.6 to 3.5 wt %, for example 1.7 to 3.0 wt % or 1.8 to 2.8 wt %. This ensures that a good impact property is obtained.

The content of 1-hexene derived units in the polypropylene composition according to the invention is 1.7 to 4.0 wt %, for example 1.8 to 3.0 wt %. This ensures a long time to brittle failure.

The ratio of the content of ethylene derived units to the content of 1-hexene derived units is at least 0.70, preferably at least 0.80, more preferably at least 0.90, and preferably at most 3.0, preferably at most 2.5. This leads to a good balance of the impact property and the time to brittle failure.

Preferably, the content of ethylene derived units in the polypropylene composition in wt % is larger than the content of 1-hexene derived units in the polypropylene composition in wt %-0.20 wt %. More preferably, the content of ethylene derived units in the polypropylene composition in wt % is larger than the content of 1-hexene derived units in the polypropylene composition in wt %-0.10 wt %. More preferably, the content of ethylene derived units in the polypropylene composition in wt % is larger than the content of 1-hexene derived units in the polypropylene composition in wt %.

Preferably, the ratio of the content of ethylene derived units in the first terpolymer to the content of ethylene derived units in the second terpolymer in the composition according to the invention is at least 0.10, preferably at least 0.20, more preferably at least 0.30, and preferably at most 2.0, preferably at most 1.5.

Preferably, the ratio of the content of 1-hexene derived units in the first terpolymer fraction to the content of 1-hexene derived units in the second terpolymer fraction in the composition according to the invention is at least 0.75, preferably at least 0.80, more preferably at least 0.90, more preferably at least 1.0, and preferably at most 5.0, more preferably at most 4.0.

Preferably, the weight ratio of the first terpolymer fraction to the second terpolymer fraction in the composition according to the invention is 0.20 to 5.0, for example 0.25 to 4.0.

Preferably, the weight average molecular weight of the polypropylene composition according to the invention is 500 to 1500 kg/mol, more preferably 650 to 1100 kg/mol as measured according to ASTM D6474-12. Further details of the measurement method are described in the experimental section.

Preferably, the numeric average molecular weight of the polypropylene composition according to the invention is 30 to 110 kg/mol, more preferably 40 to 100 kg/mol measured according to according to ASTM D6474-12. Further details of the measurement method are described in the experimental section.

Preferably, the ratio of weight average molecular weight to numeric average molecular weight (Mw/Mn) of the composition according to the invention is 7.0 to 25.0, preferably 8.0 to 20.0. Such a relatively high Mw/Mn leads to a good processability.

Preferably, the polypropylene composition according to the invention has an XS of at most 10 wt % based on the polypropylene composition. XS stands for the amount of xylene solubles which are measured using the conditions as described in the experimental section of the present application.

Preferably, the polypropylene composition according to the invention has $<G_p>/Y$ of at least 7.0, more preferably at least 7.5, more preferably at least 8.0, wherein $<G_p>$ is strain hardening modulus and Y is yield stress and $<G_p>/Y$ is determined by:

a) providing a specimen of the composition by compression molding a sheet from the composition according to ISO 1873-2 to a thickness of 0.3 mm±0.025 mm and punching a specimen having a geometry of the test specimen described in ISO/DIS 18488 from the sheet, wherein the sheet is annealed after the compression molding and before the punching at a temperature of 100° C. for 1 hour and cooled down to room temperature, b) elongating the specimen at a constant traverse speed of 20 mm/min at 100° C., c) measuring the load sustained by the specimen during the elongation to obtain a stress-strain curve and measuring the yield stress Y, d) calculating true stress-true strain curve from the stress strain curve obtained by step c) and calculating the tensile strain hardening modulus $<G_p>$ from the true stress-strain curve, according to the method as described in ISO/DIS 18488 and e) calculating a quotient of the tensile strain hardening modulus <$G_p$> divided by the yield stress Y.

Preferably, the polypropylene composition according to the invention has a polydispersity index (PI) of 5.0 to 15.0, more preferably 6.5 to 12.0. The determination method of the polydispersity index is described in the experimental section. Such a relatively high PI leads to a good processability.

Preferably, the polypropylene composition of the invention has a flexural modulus in perpendicular orientation of at least 800 MPa, preferably at least 900 MPa, as measured according to ASTM D790-10.

Preferably, the polypropylene composition of the invention has an Izod notched impact strength in perpendicular orientation of at least 5.5 kJ/m$^2$, more preferably at least 6.0 kJ/m$^2$ as measured at 23° C. according to ISO 180:2000 4A, Test geometry: 65*12.7*3.2 mm, notch 45° according to ISO 37:2011/2 parallel orientation.

By "the first and second set of reaction conditions are different", it is meant that the first set of reaction conditions and the second set of reaction conditions differ in one or more conditions chosen from the group of pressure, temperature, propylene concentration, ethylene concentration, 1-hexene concentration, hydrogen concentration, catalyst composition and catalyst concentration.

Preferably, the first set of reaction conditions and the second set of reaction conditions differ at least in the hydrogen concentration, the ethylene concentration and the 1-hexene concentration.

The invention further provides a process for the preparation of the polypropylene composition according to the invention, comprising preparing the terpolymer composition according to the invention by a process comprising the steps of preparing the first terpolymer fraction by polymerizing propylene, ethylene and 1-hexene in the presence of a Ziegler-Natta catalyst system using a first set of reaction conditions, preparing the second terpolymer fraction by polymerizing propylene, ethylene and 1-hexene in the presence of a Ziegler-Natta catalyst system using a second set of reaction conditions, wherein the first set of reaction conditions and the second set of reaction conditions differ in one or more conditions chosen from the group of pressure, temperature, propylene concentration, ethylene concentration, 1-hexene concentration, hydrogen concentration, catalyst composition and catalyst concentration.

The process for the preparation of the polypropylene composition according to the invention may further comprise mixing the terpolymer composition with additives.

The Ziegler-Natta catalyst system comprises a solid, titanium-containing component in combination with at least one aluminum alkyl cocatalyst, and preferably an external donor. Examples of the suitable catalyst systems are described in WO2011/155999, on page 7, line 16 to page 10, line 6; and page 10, line 31 to page 13, line 14 incorporated herein by reference.

Further examples of the suitable catalyst systems are described in WO2018059955. The preferred Ziegler-Natta catalyst system comprises a procatalyst, a co-catalyst and optionally an external electron donor, wherein the procatalyst id obtained by a process comprising the steps of Step A) providing or preparing a compound $R^4_z MgX^4_{2-z}$ wherein $R^4$ is independently selected from linear, branched or cyclic hydrocarbyl group independently selected from alkyl, alkenyl, aryl, aralkyl, or alkylaryl groups, and one or more combinations thereof; wherein said hydrocarbyl group may be substituted or unsubstituted, may contain one or more heteroatoms and preferably has from 1 to 20 carbon atoms;

$X^4$ is independently selected from the group consisting of fluoride (F—), chloride (Cl—), bromide (Br—) or iodide (I—), preferably chloride;

z is in a range of larger than 0 and smaller than 2, being 0<z<2;

Step B) contacting the compound $R^4_z MgX^4_{2-z}$ with a silane compound $Si(OR^5)_{4-n}(R^6)_n$ to give a first intermediate reaction product, being a solid $Mg(OR^1)_x X^1_{2-x}$ wherein $R^1$, $R^5$ and $R^e$ are each independently selected from linear, branched or cyclic hydrocarbyl group independently selected from alkyl, alkenyl, aryl, aralkyl, alkoxycarbonyl or alkylaryl groups, and one or more combinations thereof; wherein said hydrocarbyl group may be substituted or unsubstituted, may contain one or more heteroatoms and preferably has from 1 to 20 carbon atoms;

$X^1$ is independently selected from the group consisting of fluoride (F—), chloride (Cl—), bromide (Br—) or iodide (I—), preferably chloride;

n is in range of 0 to 4, preferably n is from 0 up to and including 1;

z is in a range of larger than 0 and smaller than 2, being 0<z<2;

x is in a range of larger than 0 and smaller than 2, being 0<x<2;

Step C) activating said solid support, comprising two sub steps:

Step C1) a first activation step by contacting the first intermediate reaction product obtained in step B) with at least one first activating compound being a metal alkoxide compound of formula $M^1(OR^2)_{v-w}(OR^3)_w$ or $M^2(OR^2)_{v-w}(R^3)_w$; wherein: $M^1$ is a metal selected from the group consisting of Ti, Zr, Hf, Al or Si; $M^2$ is a metal being Si; v is the valency of $M^1$ or $M^2$ and w is smaller than v; $R^2$ and $R^3$ are each a linear, branched or cyclic hydrocarbyl group independently selected from alkyl, alkenyl, aryl, aralkyl, alkoxycarbonyl or alkylaryl groups, and one or more combinations thereof; wherein said hydrocarbyl group may be substituted or unsubstituted, may contain one or more heteroatoms, and preferably has from 1 to 20 carbon atoms; and a second activating compound being an activating electron donor; and Step C2) a second activation step by contacting the activated solid support obtained in step C1) with an activating electron donor; to obtain a second intermediate reaction product;

Step D) reacting the second intermediate reaction product obtained step C2) with a halogen-containing Ti-compound, optionally an activator prior to or simultaneous with the addition of an internal donor, and at least one internal electron donor to obtain said procatalyst.

The further preferred examples of the procatalyst are mentioned in the claims of WO2018059955, incorporated by reference. Particularly preferred procatalyst is catalyst H used in Example 8 of WO2018059955.

These catalyst systems of WO2018059955 are phthalate-free. This has the advantage that undesired phthalates will not end up in the drinking water transported by a pipe made by the composition according to the invention. Therefore, preferably, the composition of the invention as well as any articles comprising such composition, such as the pipes of the invention, are essentially phthalate-free. For purposes of the invention, essentially phthalate-free is defined as the presence of less than 0.0001 wt % of phthalates based on the composition, preferably 0.00000 wt % of phthalates based on the composition.

Preferably, one or both (preferably both) of the first terpolymer fraction and the second terpolymer fraction are prepared using the Ziegler-Natta catalyst system according to the catalyst system of claim 12 of WO2018059955.

The hydrogen concentrations in the reaction conditions may be selected according to known criteria such that desired molecular weights of the respective fractions are obtained.

The amounts of ethylene and 1-hexene with respect to the amount of propylene to be fed to the reactor may be selected according to known criteria such that desired amounts of ethylene and 1-hexene in the respective polymer fractions are obtained.

Conditions for the polymerization, such as temperature and time, pressures of the monomers, avoidance of contamination of catalyst and the use of additives to molecular weights are known to the skilled person. The temperature should be selected to ensure reasonable copolymerization rates and avoid unduly long reactor residence times, but not so high as to result in the production of unreasonably high levels of stereorandom products due to excessively rapid polymerization or copolymerization rates. Generally, temperatures range from about 0° to about 120° C. with a range of from about 20° C. to about 95° C. being preferred from the standpoint of attaining good catalyst performance and high production rates. More preferably, polymerization according to this invention is carried out at temperatures ranging from about 50° C. to about 80° C.

Olefin copolymerization according to this invention is carried out at monomer pressures of about atmospheric or above. Generally, monomer pressures range from about 1.2 to about 40 bar (120 to 4000 kPa), more typically 18 to 26 bar.

The copolymerization time will generally range from about ½ to several hours in batch processes with corresponding average residence times in continuous processes.

Prepolymerization or encapsulation of the catalyst or catalyst component of this invention also may be carried out prior to being used in the polymerization or copolymerization of alpha olefins. A particularly useful prepolymerization procedure is described in U.S. Pat. No. 4,579,836, which is incorporated herein by reference.

After polymerization, polymer powder is removed from the polymerization reactor by methods known to the art, and preferably transferred to a polymer finishing apparatus in which suitable additives are incorporated into the polymer, which is heated, typically by mechanical shear and added heat, in an extruder to above melt temperature, extruded through a die, and formed into discrete pellets. Before processed by the extruder, polymer powder may be contacted with air or water vapor to deactivate any remaining catalytic species.

Single Reactor

The polypropylene composition according to the invention may be prepared by a process comprising preparing the first terpolymer fraction and the second terpolymer fraction in a single reactor to obtain the terpolymer composition. Preferably, the reactor is a gas-phase reactor, more preferably the reactor is a horizontal stirred reactor.

In a preferred embodiment, the terpolymer composition according to the invention is made by a process for polymerization of propylene, ethylene and 1-hexene in the presence of a catalyst system in a horizontal stirred reactor comprising an agitated bed for forming polymer particles,
a plurality of liquid feed ports that are subsequently arranged along a top side of the reactor above the agitated bed, the plurality of liquid feed ports comprising a first set of the liquid feed ports and a second set of the liquid feed ports arranged subsequent to the first set of the liquid feed ports in a downstream direction of the process, and
a plurality of gas feed ports that are subsequently arranged along a bottom side of the reactor below the agitated bed, the plurality of gas feed ports comprising a first set of gas feed ports and a second set of gas feed ports arranged subsequent to the first set of gas feed ports in the downstream direction of the process,
wherein the process comprises the steps of:
recovering a reactor off-gas comprising $H_2$, propylene, ethylene, 1-hexene from the reactor,
feeding the reactor off-gas to a condenser to form a gas-liquid mixture,
feeding the gas-liquid mixture to a separator to obtain a first gas stream comprising $H_2$, ethylene and propylene and a first liquid stream comprising $H_2$, ethylene, propylene and 1-hexene, wherein fresh propylene is further fed to the separator and/or added to the first liquid stream,
feeding the catalyst system to the reactor through a port arranged on the top side of the reactor,
feeding a $H_2$ poor quench liquid comprising propylene to the reactor through the first set of the liquid feed ports,
feeding a $H_2$ rich quench liquid comprising $H_2$, ethylene and propylene and 1-hexene to the reactor through the second set of liquid feed ports, wherein the $H_2$ rich quench liquid comprises at least part of the first liquid stream,
feeding a $H_2$ poor bottom gas comprising fresh propylene through the first set of gas feed ports,
feeding a $H_2$ rich bottom gas comprising $H_2$, ethylene and propylene through the second set of gas feed ports, wherein the $H_2$ rich bottom gas comprises at least part of the first gas stream, and
collecting the polymer particles formed in the agitated bed from the reactor,
wherein
fresh ethylene is fed to the reactor by feeding the fresh ethylene to the reactor as a part of the $H_2$ poor bottom gas and/or by feeding the fresh ethylene to the separator or adding the fresh ethylene to the first gas stream and
fresh 1-hexene is fed to the reactor by feeding the fresh 1-hexene to the reactor as a part of the $H_2$ poor quench liquid and/or by feeding the fresh 1-hexene to the separator or adding the fresh 1-hexene to the first liquid stream.

Subsequent Reactors

Alternatively, the polypropylene composition according to the invention may be prepared by a process comprising producing the first terpolymer fraction and the second terpolymer fraction as a bimodal terpolymer made by polymerizing the first terpolymer fraction and subsequently polymerizing the second terpolymer fraction in the presence of the first terpolymer fraction. Accordingly, the invention provides a process for the preparation of the polypropylene composition according to the invention, wherein the process comprises a sequential polymerization process comprising at least two reactors connected in series, wherein said process comprises the steps of
preparing the first terpolymer fraction in a first reactor using the first set of conditions,
transferring said first terpolymer fraction and unreacted comonomers of the first reactor to a second reactor,
feeding propylene, ethylene and 1-hexene to said second reactor,
preparing the second terpolymer fraction in said second reactor in the presence of said first terpolymer fraction to obtain the terpolymer composition.

Preferably, each of the reactors is a gas-phase reactor, more preferably each of the reactors is a horizontal stirred reactor.

Blends

Alternatively, the polypropylene composition according to the invention may be prepared by a process comprising melt-mixing the first terpolymer fraction and the second terpolymer fraction made in different reactors to obtain the terpolymer composition.

Preferably, each of the reactors is a gas-phase reactor, more preferably each of the reactors is a horizontal stirred reactor.

In another aspect, the invention relates to the polypropylene composition obtained or obtainable by the process of the invention.

In another aspect, the invention relates to a pipe comprising the polypropylene composition of the invention, more preferably to a pipe comprising at least 90 wt %, for example at least 95 wt %, for example at least 99 wt % of the polypropylene composition of the invention based on the pipe, more preferably to a pipe consisting of the polypropylene composition of the invention.

In another aspect, the invention relates to the use of the polypropylene composition of the invention for the preparation of pipes.

In another aspect, the invention relates to a process for the preparation of the pipe of the invention, comprising the step of providing the polypropylene composition of the invention. The process may comprise a further step of subjecting the polypropylene composition according to the invention to extrusion or injection moulding.

The person skilled in the art is aware of how to operate a pipe extrusion process. For example, the pipe of the invention may be produced by first melting the polypropylene composition of the instant invention in an extruder at temperatures in the range of from 200 to 300° C. and then extruding it through an annular die and cooling it.

The extruders for producing the pipe can for example be single screw extruders with an 30 L/D of 20 to 40 or twin screw extruders or extruder cascades of homogenizing extruders (single screw or twin screw). Optionally, a melt pump and/or a static mixer can be used additionally between the extruder and the ring die head. Depending on the desired size of the pipe, ring shaped dies with diameters ranging from approximately 16 to 2000 mm and even greater are possible.

For example, the melt arriving from the extruder is first distributed over an annular cross-section via conically arranged holes and then fed to the core/die combination via a coil distributor or screen. If necessary, restrictor rings or other structural elements for ensuring uniform melt flow may additionally be installed before the die outlet. After leaving the annular die, the pipe is taken off over a calibrating mandrel, usually accompanied by cooling of the pipe by air cooling and/or water cooling, optionally also with inner water cooling.

It is noted that the invention relates to all possible combinations of features described herein, preferred in particular are those combinations of features that are present in the claims. It will therefore be appreciated that all combinations of features relating to the composition according to the invention; all combinations of features relating to the process according to the invention and all combinations of features relating to the composition according to the invention and features relating to the process according to the invention are described herein.

It is further noted that the term 'comprising' does not exclude the presence of other elements. However, it is also to be understood that a description on a product/composition comprising certain components also discloses a product/composition consisting of these components. The product/composition consisting of these components may be advantageous in that it offers a simpler, more economical process for the preparation of the product/composition. Similarly, it is also to be understood that a description on a process comprising certain steps also discloses a process consisting of these steps. The process consisting of these steps may be advantageous in that it offers a simpler, more economical process.

When values are mentioned for a lower limit and an upper limit for a parameter, ranges made by the combinations of the values of the lower limit and the values of the upper limit are also understood to be disclosed.

The invention is now elucidated by way of the following examples, without however being limited thereto.

Methods

SEC: $M_z$, $M_n$, $M_w$

Size Exclusion Chromatography (SEC) was performed on the granule samples and $M_w$, $M_n$ and $M_z$ were all measured in accordance with ASTM D6474-12 (Standard Test Method for Determining Molecular Weight Distribution and Molecular Weight Averages of Polyolefins by High Temperature Gel Permeation Chromatography). $M_w$ stands for the weight average molecular weight and $M_n$ stands for the number average weight. $M_z$ stands for the z-average molecular weight.

In addition to the method specified by ASTM D6474-12, the method was performed using a configuration in which a Polymer Char IR5 infrared concentration detector and a Polymer Char online viscosity detector was used to gain 'absolute' (and therefore more accurate) molar masses. Three columns of Polymer Laboratories 13 μm PLgel Olexis, 300×7.5 mm were used in series with 1,2,4-trichlorobenzene stabilized with 1 g/L butylhydroxytoluene (also known as 2,6-di-tert-butyl-4-methylphenol or BHT) as eluent.

The molar mass distribution and derived molar mass averages were determined based on a calibration using linear PE standards (narrow and broad ($M_w/M_n$=4 to 15)) in the range of 0.5-2800 kg/mol. Samples of polymer granules were mixed with Tris(2,4-di-tert-butylphenyl)phosphite (Irgafos 168) and 1,1,3-Tris(2-methyl-4-hydroxy-5-tert-butylphenyl)butane (Topanol CA) in a weight ratio of sample: Irgafos: Topanol of 1:1:1, after which the mixture thus obtained was dissolved in 1,2,4-trichlorobenzene stabilized with 1 g/L BHT until the concentration of the mixture in 1,2,3-trichlorobenzene stabilized with 1 g/L BHT was 0.03 wt %.

Xylene Solubles (XS)

Powder samples were evaluated for XS, wt % xylene solubles. 1 gram of polymer and 100 ml of xylene are introduced in a glass flask equipped with a magnetic stirrer. The temperature is raised up to the boiling point of the solvent. The so obtained clear solution is then kept under reflux and stirring for further 15 min. Heating is stopped and the isolating plate between heating and flask is removed. Cooling takes place with stirring for 5 min. The closed flask is then kept for 30 min in a thermostatic water bath at 25° C. for 30 min. The so formed solid is filtered on filtering paper. 25 ml of the filtered liquid is poured in a previously weighed aluminium container, which is heated in a stove of 140° C. for at least 2 hours, under nitrogen flow and vacuum, to remove the solvent by evaporation. The container is then kept in an oven at 140° C. under vacuum until constant weight is obtained. The weight percentage of polymer soluble in xylene at room temperature is then calculated.

13C-NMR for C2, C6 Comonomer Content

Approximately 150 mg of sample was dissolved at ~135° C. in ~3 ml of 1,1,2,2-tetrachloroethane-d2 (TCE-d2)/BHT stock solution using a 10 mm NMR tube. The stock solution was made by dissolving ~5 mg on BHT in 25 ml of TCE-d2. Oxygen concentration in the tube was reduced by flushing the tube for ~1 min with nitrogen before dissolution. The sample was periodically checked for homogeneity and manually mixed as necessary.

All NMR experiments were carried out on a Bruker 500 Avance III HD spectrometer equipped with a 10 mm DUAL (proton and carbon) cryogenically cooled probe head operating at 125° C. The 13C NMR measurements were performed using a spectral width of 220 ppm, an acquisition time of ~1.4 s and a relaxation delay of 20 s between each of the 512 transients. The spectra were calibrated by setting the central signal of TCE's triplet at 74.2 ppm.

Commoner content was calculated as described in: F. F. N. Escher, G. B. Galland, J Polym Sci Part A: Polym Chem 42: 2474-2482, 2004

Dynamic Mechanical Spectroscopy (DMS) Analysis for PI (Polydispersity Index)

Compression moulding of the samples was done at 200° C. in consecutive steps; at 0 bar for 1 minute, at 5 bars for 1 minute, at 40 bars for 3 minutes and was completed by a cooling step at 40 bars. The rheological behavior of the samples was studied using a DHR2 torsional rheometer (TA Instruments) equipped with a parallel plate geometry (diameter=25 mm, gap=1000 μm). The rheological profiles were obtained by conducting oscillation frequency sweep experiments. The measurements were performed with the following procedure:

a) Conditioning step at 230° C. for 60 seconds
b) Oscillation frequency sweep at 230° C.: frequency 600-0.01 rad/s, 1% strain, logarithmic sweep, 5 pts/decade.

Distorted torque-displacement data points were determined for each sample. Using the Cox-Merz rule and the Trios software, the undistorted rheology data collected in oscillation mode were transformed to the ones in flow mode. The transformed rheological curves were fitted using Yasuda-Carreau model from which a zero-shear viscosity value was obtained. From these, the rheology polydispersity index (PI) of the blends was determined by dividing the cross-over modulus (which occurs when the storage (G') and loss (G") moduli are equal) into 105 Pa as per definition. This is a convenient measure of polydispersity that is often employed. The PI value could be determined for all polymer blends without the need of extrapolating the cross-over point. PI is calculated as follows:

$PI = 10^5\ Pa/G_c$ where $G_c$ occurs when $(G')$ storage modulus=$(G")$ loss modulus Melt Flow Rate (MFR)

For purpose of the invention the melt flow rate is the melt flow rate as measured according to ISO 1133-1-2011 (2.16 kg/230° C.).

<Gp>/Ys

Strain hardening modulus divided by yield stress (<Gp>/Ys) were measured by the method described in WO2018/011177:

a) providing a specimen of the composition by compression molding a sheet from the composition according to ISO 1873-2 to a thickness of 0.3 mm±0,025 mm and punching a specimen having a geometry of the test specimen described in ISO/DIS 18488 from the sheet, wherein the sheet is annealed after the compression molding and before the punching at a temperature of 100° C. for 1 hour and cooled down to room temperature, b) elongating the specimen at a constant traverse speed of 20 mm/min at 100 ° C., c) measuring the load sustained by the specimen during the elongation to obtain a stress-strain curve and measuring the yield stress Y, d) calculating true stress-true strain curve from the stress strain curve obtained by step c) and calculating the tensile strain hardening modulus <$G_p$> from the true stress-strain curve, according to the method as described in ISO/DIS 18488 and e) calculating a quotient of the tensile strain hardening modulus <$G_p$> divided by the yield stress Y.

Steps b) and c) were performed as follows:

Measurement of the exact dimensions (with accuracy of 0.01 mm) of width (b) and (with an accuracy of 0.005 mm) of thickness (h) of each individual test specimen.

Conditioning of the test specimens for a period of time, e.g. at least 30 minutes, in the temperature chamber set at a predetermined temperature of 100° C. prior to starting the test.

Clamping of the test piece in the upper grip of the elongation device. The clamps are chosen to avoid damage and slippage of the test piece.

Closure of the temperature chamber.

After reaching said predetermined temperature, clamp the test piece with the lower grip.

The sample shall remain between the clamps for a certain period, e.g. at least 1 minute, before the load is applied and measurement starts.

Add a pre-stress e.g. of 0.4 MPa reached with a speed of e.g. 5 mm/min.

During the test, the load sustained by the specimen and the elongation are measured.

Extend the test specimen at a constant traverse speed of 20 mm/min until the test specimen breaks.

For step d), the method of the calculations is described in ISO/DIS 18488, section 8 "Data treatment".

The draw ratio, λ, is calculated from the length, l, and the gauge length, $l_0$, as shown by formula 1.

$$\lambda = \frac{l}{l_0} = 1 + \frac{\Delta l}{l_0} \qquad (1)$$

where

Δl is the increase in the specimen length between the gauge marks.

The true stress, $\sigma_{true}$, is calculated according to formula 2, which is derived on the assumption of conservation of volume between the gauge marks:

$$\sigma_{true} = \lambda \cdot \frac{F}{A} \quad (2)$$

where

F is the measured force (N).

It is important that the initial cross section A shall be determined for each individual test bar.

The Neo-Hookean constitutive model (formula 3, see Annex A of ISO/DIN 18488) is used to fit and extrapolate the data from which <Gp>(MPa) for 8<λ<12 is calculated.

$$\sigma_{true} = \frac{\langle G_p \rangle}{20} \cdot \left(\lambda^2 - \frac{1}{\lambda}\right)_{+C} \quad (3)$$

where

C is a mathematical parameter of the constitutive model describing the yield stress extrapolated to λ=0.

Accuracy of fit of data (R2) greater than 0.9 shall be achieved.

Flex. Modulus (Perpendicular Orientation).

For purpose of the present invention, stiffness of the granulate is determined by measuring the flexural modulus according to ASTM D790-10. Flexural modulus was determined on 3.2 mm thick specimens, injection molded according to ISO 37/2, samples tested in perpendicular orientation.

Izod Notched Impact Strength (Perpendicular Orientation)

For purpose of the present invention, impact strength is determined by measuring the Izod notched impact strength of the granulate at 23° C. according to ISO 180:2000 4A, Test geometry: 65*12.7*3.2 mm, notch 45° according to ISO 37:2011/2 perpendicular orientation.

Experiments

The catalyst used for the polymerization was catalyst H (Ex.8) of WO2018/059955. The composition of the solid catalyst H produced is given in Table 1.

TABLE 1

Composition of solid catalyst H

| Catalyst | Example | d50 [μm] | Mg [%] | Ti [%] | ID [%] | Activator (EB) [%] | EtO [%] |
|---|---|---|---|---|---|---|---|
| H | 8 | 22.16 | 19.65 | 2.40 | 8.41 | 6.68 | 1.48 |

Polymerization experiments of propylene terpolymers were performed on a bench-scale gas-phase reactor using above described catalyst and DiPDMS: di-(isopropyl)-dimethoxysilane as the external donor.

The reactor conditions and feed are described in table 2 below.

TABLE 2

Process conditions

| | | Ex. 1 | Ex. 2 | Comp 1. | Comp. 2. | Comp. 3 |
|---|---|---|---|---|---|---|
| component A (first terpolymer fraction) | | | | | | |
| Si/Ti | molar ratio | 15 | 15 | 15 | 15 | 15 |

TABLE 2-continued

Process conditions

| | | Ex. 1 | Ex. 2 | Comp 1. | Comp. 2. | Comp. 3 |
|---|---|---|---|---|---|---|
| Al/Ti | molar ratio | 50 | 50 | 50 | 50 | 50 |
| 1-hexene | gr/hr | 26 | 47 | 33 | 37 | 45 |
| T | ° C. | 66 | 66 | 66 | 66 | 66 |
| P | Bar | 21 | 21 | 21 | 21 | 21 |
| C2/C3 | mol/mol | 0.019 | 0.21 | 0.0145 | 0.018 | — |
| H2/C3 | mol/mol | 0.0022 | 0.0031 | 0.007 | 0.006 | 0.0018 |
| component B (second terpolymer fraction) | | | | | | |
| Si/Ti | molar ratio | 15 | 15 | | | 15 |
| Al/Ti | molar ratio | 50 | 50 | | | 50 |
| 1-hexene | gr/hr | 21 | 9 | | | — |
| T | C. | 66 | 66 | | | 66 |
| P | Bar | 21 | 21 | | | 21 |
| C2/C3 | mol/mol | 0.02 | 0.026 | | | 0.028 |
| H2/C3 | mol/mol | 0.024 | 0.031 | | | 0.024 |

For examples 1, 2 and comparative experiment 3, powder of component A and powder of component B were obtained separately. A blend was made by melt-mixing the powders in a double screw extruder together with additives. For comparative experiments 1, 2, only one type of powder was obtained and was mixed in a double screw extruder together with additives. The additives (antioxidants, acid scavengers) were used in an amount of 1.05 wt % based on the powder and mixed prior to dosing to the extruder. The temperature profile in the extruder was 30-30-80-100-130-180-230-230-240° C., at a throughput of 1 kg/h at 200 rpm.

TABLE 3

Results

| Exp Nr. | | Ex. 1 | Ex. 2 | Comp 1. | Comp 2. | Comp. 3 |
|---|---|---|---|---|---|---|
| PP-A /PP-B | wt %/wt % | 1 | 1.22 | | | 1 |
| A + B | wt % | 100 | 100 | | | 100 |
| TC6 | wt % | 2 | | | | |
| TC2 | wt % | 2.1 | 2.4 | 1.8 | 1.5 | 1.8 |
| TC2 (A) | wt % | 2.1 | 2 | | | 0 |
| TC2 (B) | wt % | 2.1 | 2.9 | | | 4 |
| C2 (A)/C2 (B) | wt %/wt % | 1.0 | 0.7 | | | 0.0 |
| TC6 | wt % | 2.1 | 1.9 | 2 | 2.5 | 2.02 |
| TC6 (A) | wt % | 2.1 | 3 | | | 3.96 |
| TC6 (B) | wt % | 2.1 | 0.9 | | | 0 |
| C6 (A)/C6 (B) | wt %/wt % | 1.0 | 3.3 | | | ∞ |
| TC2/TC6 | wt %/wt % | 1 | 1.26 | 0.9 | 0.6 | 0.89 |
| Part A MFI 5 Gran | dg/min | 0.22 | 0.22 | | | 0.2 |
| Part B MFI 2.16 Gran. | dg/min | 1.4 | 1.91 | | | 1.4 |
| Overall MFI 2.16 Gran | dg/min | 0.19 | 0.19 | 0.18 | 0.16 | 0.18 |
| XS | wt % | | | | 5.4 | |
| Mn | kg/mol | 65 | 55 | 57 | | 60 |

TABLE 3-continued

Results

| Exp Nr. | | Ex. 1 | Ex. 2 | Comp 1. | Comp 2. | Comp. 3 |
|---|---|---|---|---|---|---|
| Mw | kg/mol | 930 | 1100 | 740 | | 960 |
| Mz | kg/mol | 3900 | 6200 | 2900 | | 4900 |
| Mw/Mn | — | 14.4 | 19.6 | 13.1 | | 15.8 |
| PI | | 6.9 | 7.6 | 6.2 | | 8.1 |
| MFI 5 kg gran | dg/min | 1.07 | 1 | 0.91 | 0.86 | 1.11 |
| MFI 10 kg gran | dg/min | 5.6 | 5.43 | 4.69 | 4.5 | 6.11 |
| <Gp>/Ys @100° C. | — | 8.8 | 8.1 | 7.81 | 8.00 | 6.2 |
| Flexural ASTM D790 (L) @ 23° C. | MPa | 1078.0 | 957.0 | 1135.0 | 1088.0 | 1129.0 |
| Izod ISO 180/4A (L) @ 23° C. | kJ/m2 | 6.1 | 9.2 | 5.6 | 4.8 | 5.9 |

The examples according to the invention Ex. 1 and 2 as compared to the comparative examples show an improved impact resistance (Izod) while maintaining the flexural modulus and the time to brittle failure (as indicated by a high <Gp>/Ys, which is an indication for the time to brittle failure as explained in WO2018/011177).

The granules are used to extrude a pipe of 32*3.0 mm on a Reifenhauser S 50/30D/I- and S 50/30 D/II-Extruder according to ISO 1167-2:2006.

Hydrostatic pipe testing is carried out according to ISO 1167-1:2006 at 95° C. and the hours after which the pipe failed under a hoop stress of either 4.2, 4.5 and 4.9 MPa (measured according to ISO3213:2009) are noted. The pipes made of the compositions of the examples according to the invention Ex. 1 and 2 show a longer time to failure as compared to the pipes made of the compositions according to comparative examples.

The invention claimed is:

1. A polypropylene composition comprising a terpolymer composition comprising (A) a first terpolymer fraction containing propylene, ethylene and 1-hexene, wherein the first terpolymer fraction has a melt flow rate of 0.030 to 1.0 dg/min determined by ISO 1133-1:2011 (230° C., 5 kg) and (B) a second terpolymer fraction containing propylene, ethylene and 1-hexene, wherein the second terpolymer fraction has a melt flow rate of 0.30 to 70 dg/min determined by ISO 1133-1:2011 (230° C., 2.16 kg),
  wherein the first terpolymer fraction is prepared using a first set of reaction conditions, the second terpolymer fraction is prepared using a second set of reaction conditions and the first and second set of reaction conditions are different, wherein the polypropylene composition
  (i) has a melt flow rate of 0.10 to 0.70 dg/min determined by ISO 1133-1:2011 (230° C., 2.16 kg);
  (ii) has a content of ethylene derived units in the range from 1.6 to 3.5 wt %;
  (iii) has a content of 1-hexene derived units in the range from 1.7 to 4.0 wt %; and
  wherein the content of ethylene derived units in the polypropylene composition in wt % is larger than the content of 1-hexene derived units in the polypropylene composition in wt %-0.10 wt %; and
  wherein the composition has <Gp>/Y of at least 7.5, wherein <Gp> is strain hardening modulus and Y is yield stress and <Gp>/Y is determined by:
    a) providing a specimen of the composition by compression molding a sheet from the composition according to ISO 1873-2 to a thickness of 0.3 mm±0.025 mm and punching a specimen having a geometry of the test specimen described in ISO/DIS 18488 from the sheet, wherein the sheet is annealed after the compression molding and before the punching at a temperature of 100° C. for 1 hour and cooled down to room temperature,
    b) elongating the specimen at a constant traverse speed of 20 mm/min at 100° C.
    c) measuring the load sustained by the specimen during the elongation to obtain a stress-strain curve and measuring the yield stress Y,
    d) calculating true stress-true strain curve from the stress strain curve obtained by step c) and calculating the tensile strain hardening modulus <Gp> from the true stress-strain curve, according to the method as described in ISO/DIS 18488 and
    e) calculating a quotient of the tensile strain hardening modulus <Gp> divided by the yield stress Y.

2. The polypropylene composition according to claim 1, wherein the melt flow rate of the polypropylene composition determined by ISO 1133-1:2011 (230° C., 2.16 kg) is in the range from 0.10 to 0.50 dg/min.

3. The polypropylene composition according to claim 1, wherein the content of ethylene derived units in the polypropylene composition is 1.7 to 3.0 wt %.

4. The polypropylene composition according to claim 1, wherein the content of 1-hexene derived units in the polypropylene composition is 1.8 to 3.0 wt %.

5. The polypropylene composition according to claim 1, wherein the content of ethylene derived units in the polypropylene composition in wt % is larger than the content of 1-hexene derived units in the polypropylene composition in wt %.

6. The polypropylene composition according to claim 1, wherein the weight ratio of the first terpolymer fraction to the second terpolymer fraction in the polypropylene composition is 0.20 to 5.0.

7. The polypropylene composition according to claim 1, wherein the ratio of weight average molecular weight to numeric average molecular weight (Mw/Mn) of the composition is in the range from 7.0 to 25.0, wherein the Mw and Mn are measured according to ASTM D6474-12, and/or wherein the polypropylene composition has a polydispersity index (PI) of 5.0 to 15.0.

8. The polypropylene composition according to claim 1, wherein the composition has <Gp>/Y of at least 8.0.

9. The polypropylene composition according to claim 1, wherein the polypropylene composition comprises additives and the sum of the amounts of the first terpolymer, the second terpolymer and the additives is 100 wt % of the polypropylene composition.

10. A process for the preparation of the polypropylene composition according to claim 1, comprising preparing the terpolymer composition by a process comprising the steps of
  preparing the first terpolymer fraction by polymerizing propylene, ethylene and 1-hexene in the presence of a Ziegler-Natta catalyst system using a first set of reaction conditions,
  preparing the second terpolymer fraction by polymerizing propylene, ethylene and 1-hexene in the presence of a Ziegler-Natta catalyst system using a second set of reaction conditions,
  wherein the first set of reaction conditions and the second set of reaction conditions differ in one or more conditions chosen from the group of pressure, temperature, propylene concentration, ethylene concentration, 1-hexene concentration and hydrogen concentration.

11. The process according to claim 10, wherein the first terpolymer fraction and the second terpolymer fraction are prepared in a single reactor to obtain the terpolymer composition.

12. The process according to claim 10, wherein the Ziegler-Natta catalyst system comprises a procatalyst, a co-catalyst and optionally an external electron donor, wherein the procatalyst id obtained by a process comprising the steps of Step A) providing or preparing a compound R4zMgX42-z wherein
  R4 is independently selected from linear, branched or cyclic hydrocarbyl group independently selected from alkyl, alkenyl, aryl, aralkyl, or alkylaryl groups, and one or more combinations thereof; wherein said hydrocarbyl group may be substituted or unsubstituted, may contain one or more heteroatoms;
  X4 is independently selected from the group consisting of fluoride (F—), chloride (CI—), bromide (Br—) or iodide (I—);
  z is in a range of larger than 0 and smaller than 2, being 0<z<2;

Step B) contacting the compound R4zMgX42-z with a silane compound Si(OR5)4-n(R6)n to give a first intermediate reaction product, being a solid Mg(OR1)xX12-x wherein
  R1, R5 and R6 are each independently selected from linear, branched or cyclic hydrocarbyl group independently selected from alkyl, alkenyl, aryl, aralkyl, alkoxycarbonyl or alkylaryl groups, and one or more combinations thereof; wherein said hydrocarbyl group may be substituted or unsubstituted, may contain one or more heteroatoms;
  X1 is independently selected from the group consisting of fluoride (F—), chloride (CI—), bromide (Br—) or iodide (I—);
  n is in range of 0 to 4;
  z is in a range of larger than 0 and smaller than 2, being 0<z<2;
  x is in a range of larger than 0 and smaller than 2, being 0<x<2;

Step C) activating said solid support, comprising two sub steps:

Step C1) a first activation step by contacting the first intermediate reaction product obtained in step B) with at least one first activating compound being a metal alkoxide compound of formula M1(OR2)v-w(OR3)w or M2(OR2)v-w(R3)w; wherein: M1 is a metal selected from the group consisting of Ti, Zr, Hf, Al or Si; M2 is a metal being Si; v is the valency of M1 or M2 and w is smaller than v; R2 and R3 are each a linear, branched or cyclic hydrocarbyl group independently selected from alkyl, alkenyl, aryl, aralkyl, alkoxycarbonyl or alkylaryl groups, and one or more combinations thereof; wherein said hydrocarbyl group may be substituted or unsubstituted, may contain one or more heteroatoms; and a second activating compound being an activating electron donor; and Step C2) a second activation step by contacting the activated solid support obtained in step C1) with an activating electron donor; to obtain a second intermediate reaction product;

Step D) reacting the second intermediate reaction product obtained step C2) with a halogen-containing Ti-compound, optionally an activator prior to or simultaneous with the addition of an internal donor, and at least one internal electron donor to obtain said procatalyst.

13. An article comprising the polypropylene composition according to claim 1.

14. The article of claim 13, wherein the article is a pipe.

15. A pipe comprising a polypropylene composition comprising a terpolymer composition; wherein the terpolymer composition comprises:

(A) a first terpolymer fraction containing propylene, ethylene and 1-hexene, wherein the first terpolymer fraction has a melt flow rate of 0.030 to 1.0 dg/min determined by ISO 1133-1:2011 (230° C., 5 kg) and (B) a second terpolymer fraction containing propylene, ethylene and 1-hexene, wherein the second terpolymer fraction has a melt flow rate of 0.30 to 70 dg/min determined by ISO 1133-1:2011 (230° C., 2.16 kg), wherein the weight ratio of the first terpolymer fraction to the second terpolymer fraction in the polypropylene composition is 0.20 to 5.0;

wherein the first terpolymer fraction is prepared using a first set of reaction conditions, the second terpolymer fraction is prepared using a second set of reaction conditions and the first and second set of reaction conditions are different, wherein the polypropylene composition (i) has a melt flow rate of 0.10 to 0.70 dg/min determined by ISO 1133-1:2011 (230° C., 2.16 kg);

(ii) has a content of ethylene derived units in the range from 1.7 to 3.0 wt %;

(iii) has a content of 1-hexene derived units in the range from 1.8 to 3.0 wt %;

wherein the content of ethylene derived units in the polypropylene composition in wt % is larger than the content of 1-hexene derived units in the polypropylene composition in wt %-0.10 wt %; and wherein the composition has <Gp>/Y of at least 7.5, wherein <Gp> is strain hardening modulus and Y is yield stress and <Gp>/Y is determined by:

a) providing a specimen of the composition by compression molding a sheet from the composition according to ISO 1873-2 to a thickness of 0.3 mm±0.025 mm and punching a specimen having a geometry of the test specimen described in ISO/DIS 18488 from the sheet, wherein the sheet is annealed after the compression molding and before the punching at a temperature of 100° C. for 1 hour and cooled down to room temperature, b) elongating the specimen at a constant traverse speed of 20 mm/min at 100° C., c) measuring the load sustained by the specimen during the elongation to obtain a stress-strain curve and measuring the yield stress Y, d) calculating true stress-true strain curve from the stress strain curve obtained by step c) and calculating the tensile strain hardening modulus <Gp> from the true stress-strain curve, according to the method as described in ISO/DIS 18488 and e) calculating a quotient of the tensile strain hardening modulus <Gp> divided by the yield stress Y.

16. The polypropylene composition of claim 1, wherein the melt flow rate of the polypropylene composition determined by ISO 1133-1:2011 (230° C., 2.16 kg) is in the range from 0.10 to 0.30 dg/min.

17. The polypropylene composition of claim 1, wherein the first terpolymer fraction has a melt flow rate of 0.10 to 0.60 dg/min determined by ISO 1133-1:2011 (230° C., 5 kg), and the second terpolymer fraction has a melt flow rate of 1.0 to 30 dg/min determined by ISO 1133-1:2011 (230° C., 2.16 kg).

18. The polypropylene composition of claim 1, wherein the amount of the first terpolymer fraction is in the range from 40 to 85 wt % based on the terpolymer composition and the amount of the second terpolymer fraction is in the range from 15 to 60 wt % based on the terpolymer composition.

* * * * *